United States Patent [19]

Bolt et al.

[11] 4,377,743

[45] Mar. 22, 1983

[54] CIGARETTE ROD OPTICAL INSPECTION

[75] Inventors: Reginald C. Bolt, High Wycombe; John G. Dowding, Milton Keynes, both of England

[73] Assignee: Molins Limited, Bucks, England

[21] Appl. No.: 195,621

[22] Filed: Oct. 9, 1980

[30] Foreign Application Priority Data

Oct. 12, 1979 [GB] United Kingdom ................. 7935479

[51] Int. Cl.³ .............................................. G01V 9/04
[52] U.S. Cl. ................................. 250/223 R; 209/536
[58] Field of Search ............... 209/535, 536, 576, 577; 250/308, 358 P, 359, 222 R, 223 R, 223 B, 578, 208, 209, 216, 239, 572; 356/445, 448

[56] References Cited

U.S. PATENT DOCUMENTS

| | | | |
|---|---|---|---|
| 2,947,212 | 8/1960 | Woods | 250/572 |
| 3,851,975 | 12/1974 | Serret | 250/223 B |
| 3,890,509 | 6/1975 | Maxey | 250/223 R |
| 4,208,578 | 6/1980 | McLoughlin et al. | 209/536 |

Primary Examiner—David C. Nelms
Attorney, Agent, or Firm—Antonelli, Terry & Wands

[57] ABSTRACT

An inspection device for a continuous cigarette rod comprises a plurality of infra-red emitter-detector units circumferentially spaced around the path of a rod. The light from each unit is focussed onto and collected from a specific area of the rod. Two, or more, axially displaced arrays of units are each arranged to inspect areas of the rod which are staggered in relation to the areas inspected by the other array or arrays.

Signals from the units are multiplexed and transmitted to processing circuitry. Instantaneous signals are compared with predetermined values derived for each optical unit as a proportion of the running average of the instantaneous signal. If the instantaneous signal falls below this predetermined value a warning device is operated and the cigarette is ejected.

Known devices use expensive optical fibres requiring a close fit to the cigarette rod.

16 Claims, 4 Drawing Figures

CIGARETTE ROD OPTICAL INSPECTION

This invention relates to optical inspection of continuous cigarette rods produced by continuous cigarette making machines or the like. It has previously been proposed to inspect the surface of such rods using an assembly of fibre optic light guides to illuminate the surface of the rod and also to transmit the reflected light back to a transducer or transducers, as shown for example in GB patent specification No. 1135183. The disadvantages of such systems are that they are expensive and require the light guide ends to be fitted very close to the moving rod.

According to the present invention there is provided an inspection device for a continuous cigarette rod comprising means for guiding a continuous cigarette rod through an inspection station at which there are a number of optical units arranged at circumferentially spaced positions around the path of the rod, each optical unit comprising a light emitter and a light detector, the light emitter of each unit being arranged to provide a focussed beam of light directed at a respective area of a rod being inspected, and the light detector of each unit being arranged to receive light from the respective area.

It will be understood that the terms "optical" and "light" as used herein are intended to cover a wider spectrum of electromagnetic wavelengths than just visible light, for example, the units may be infra-red units.

Preferably, the light emitter and detector of each optical unit are packaged as a single unit i.e. an integral part, with a lens in front of each device, so arranged that when the unit is positioned at a suitable distance from the rod, the two devices will both be directed at the same area.

Preferably, output signals from the light detector devices are transmitted from the measuring head to a control unit by means of a multiplexing system, so that a sufficient number of optical units can be arranged around the rod to cover the whole circumference with good resolution, without the necessity for a large number of connections between the head and the measuring circuitry.

According to the invention there is also provided a method of inspecting cigarettes or other continuous rods of the tobacco industry comprising using a plurality of focussed light emitter-detector units spaced circumferentially around a rod being inspected, each unit being arranged to propagate focussed light onto a defined surface region of the rod and to receive the light reflected from that surface region and further arranged to generate an electrical signal related to the intensity of the received light, the method including multiplexing the intensity related signals from the various units, transferring the multiplexed signals to a control means, demultiplexing the signals and processing the signal from each unit by continually averaging the signal, comparing the averaged signal with the instantaneous signal from that unit, and generating a fault signal if the instantaneous signal differs from the averaged signals by more than a preset percentage.

One embodiment of the invention will now be described by way of example with reference to the accompanying drawings, in which.

Figure 1:
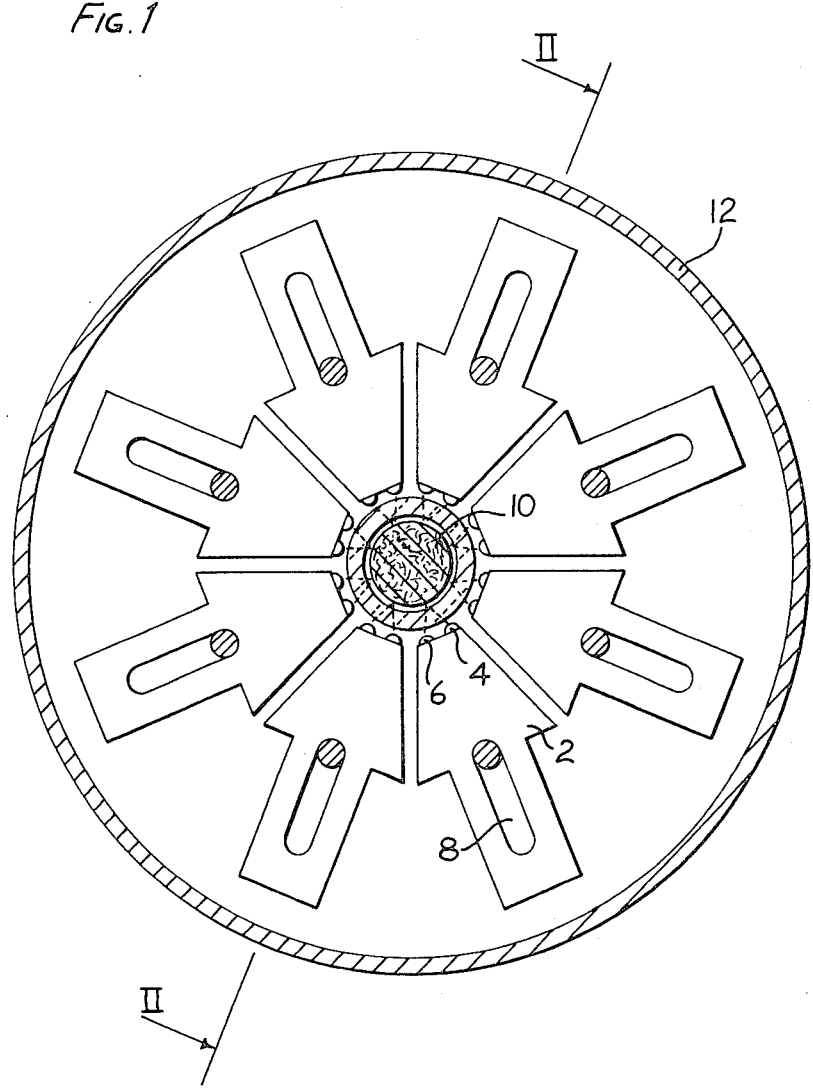
FIG. 1 is a cross-section through an optical inspection device, taken on the line I—I of FIG. 2.

Referring to FIG. 1, the measuring head of the apparatus comprises a plurality of infra-red sensor units 2 such as the Optron Inc. Type OPB 253A, which each contain a light emitting diode and a phototransistor, positioned behind respective lenses 4 and 6. The lens for the light emitting diode focusses light onto a specific area of a cigarette rod and the lens for the phototransistor collects the light reflected from that area, i.e. "focusses" the reflected light onto the phototransistor. Each unit has a flat casing which is generally wedge-shaped in plan as shown in FIG. 1, with a fixing slot 8 by means of which the unit is fixed in position. The units may be mounted to be readily removable. In the arrangement shown, there are eight units spaced in a circle around the rod, and because of the angle of view seen by each unit, and the shape of the units, it is necessary to arrange a further set of eight units at a position axially displaced from the set shown, which are arranged with their center-lines offset by 22.5° from those of the first set so that the units of each set inspect areas of rod which are staggered in relation to the areas inspected by the units of the other set, to obtain complete coverage of the surface. More than two sets may be used.

Figure 2:
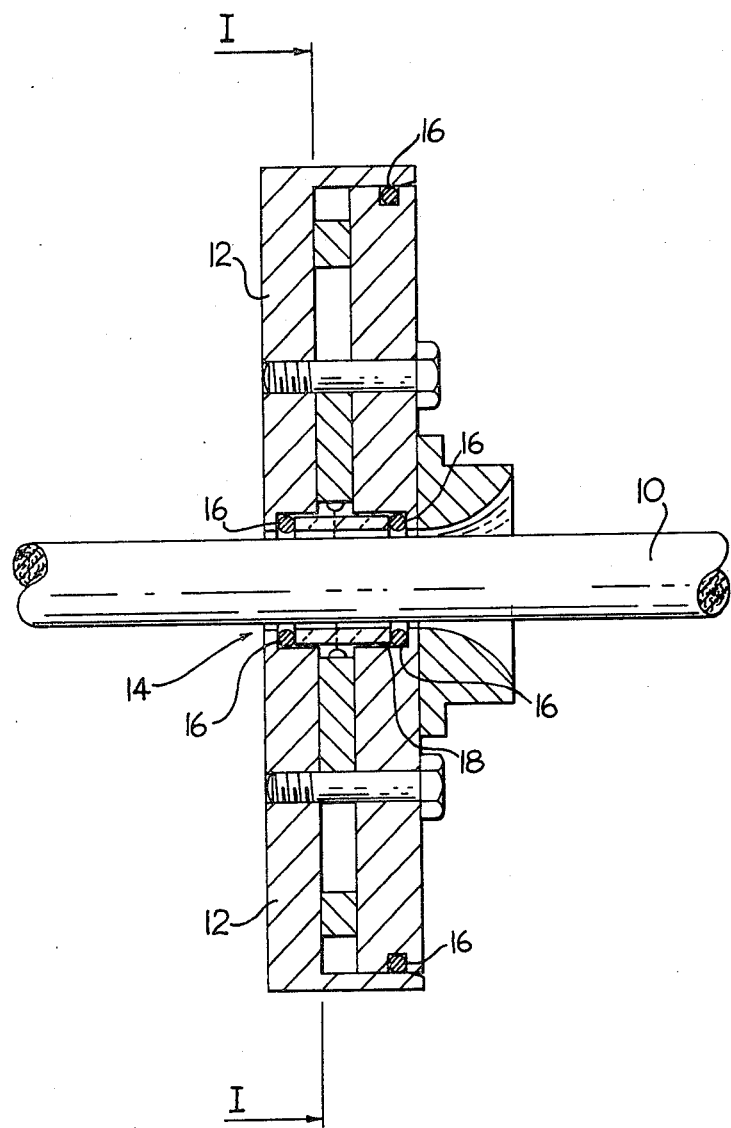
FIG. 2 is a section on line II—II of FIG. 1.

FIG. 2 shows a vertical cross-section through one of the sets of units of FIG. 1, showing the general arrangement for mounting the units relative to the cigarette rod. The units are held within a casing 12 having a central aperture 14 through which the rod 10 passes, suitable sealing rings 16 being located in the joints of the casing and around a glass cylindrical member 18 which closes the interior of the casing from the central aperture.

Figure 3:
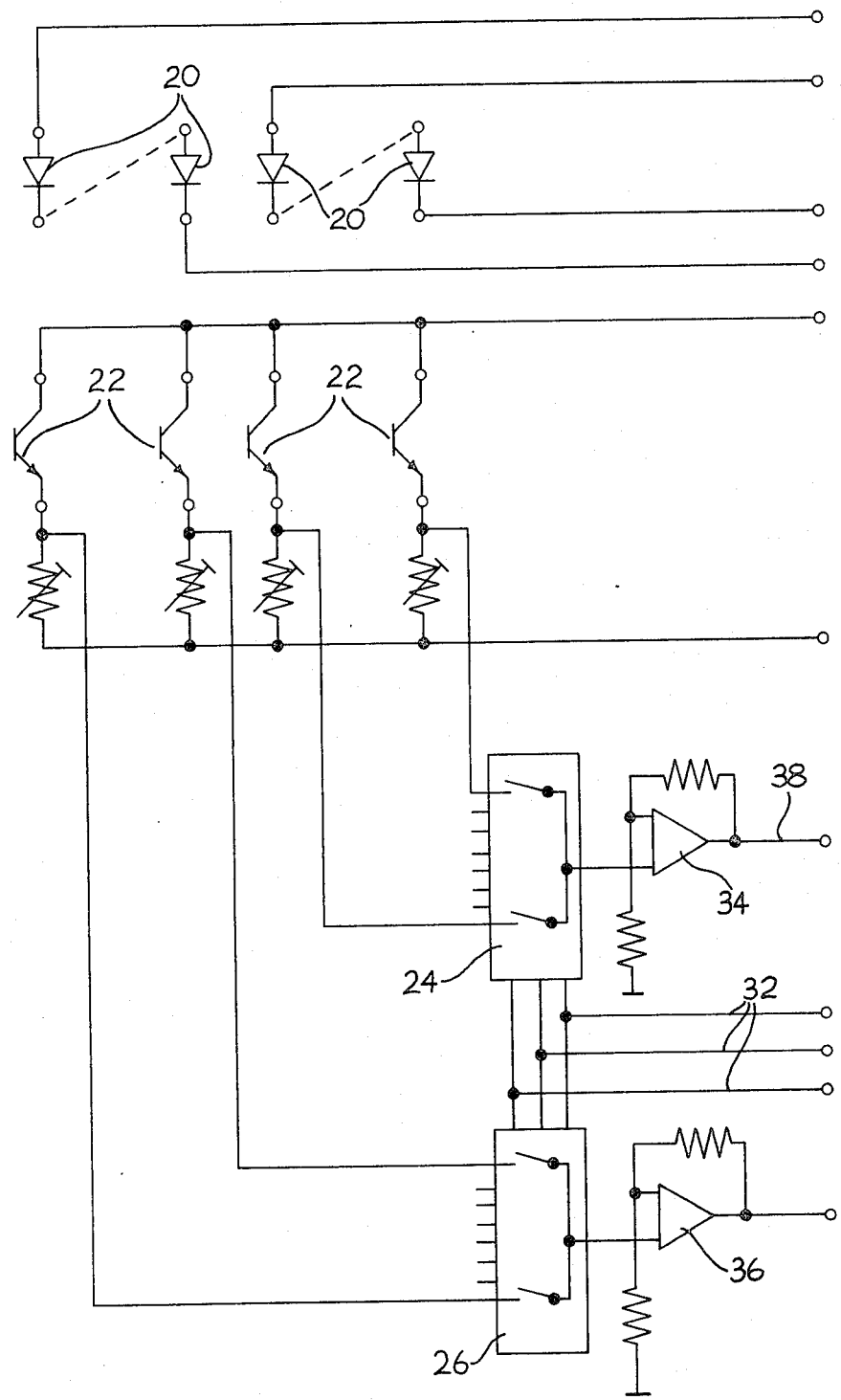
FIG. 3 is a diagram of a light-source drive circuit and a signal multiplexing circuit.
Figure 4:
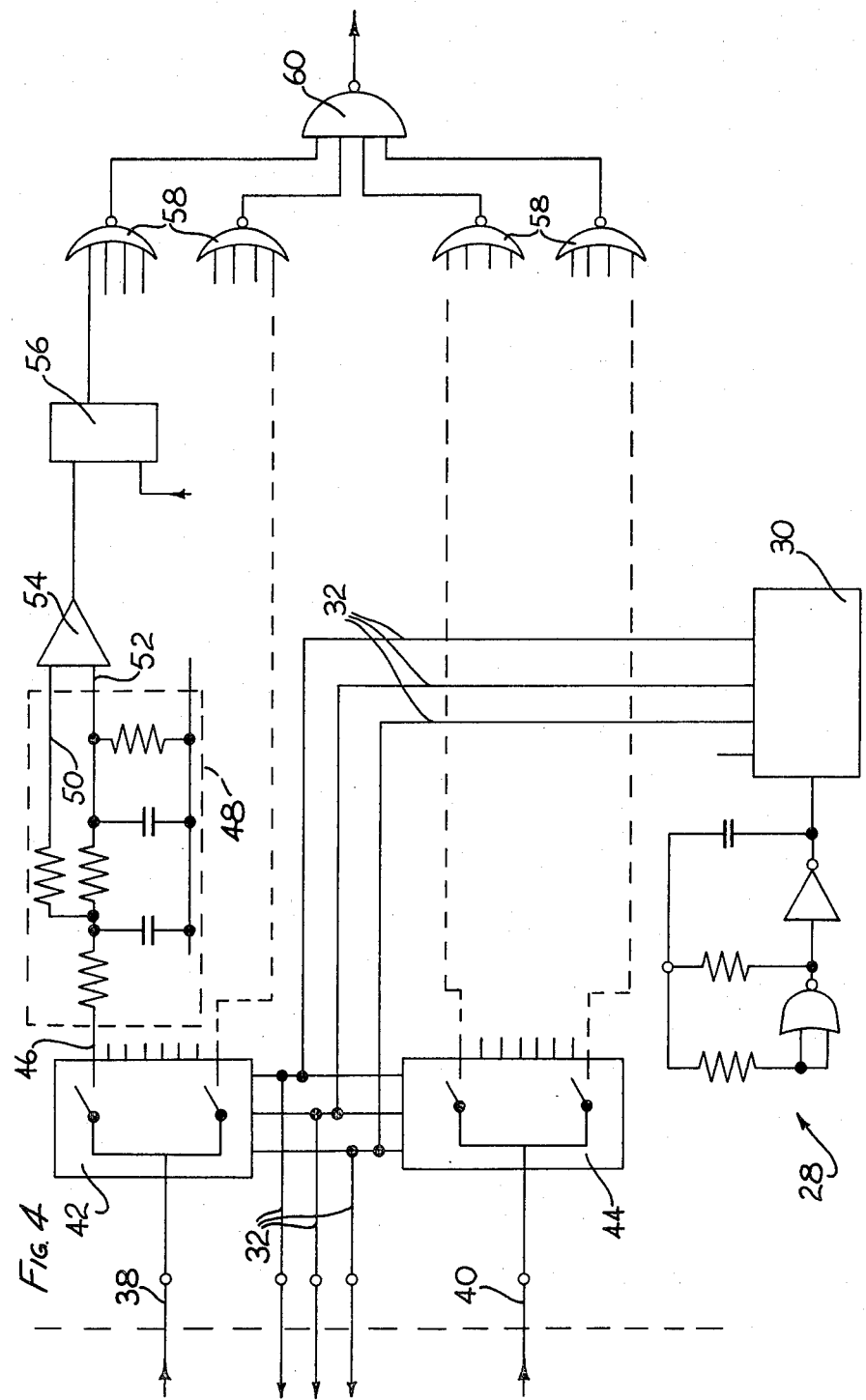
FIG. 4 is a circuit diagram of a demultiplexing and signal processing arrangement.

Referring to FIG. 3, the LED's 20 are driven in two banks of eight in series with a d.c. current source, whilst the photodetectors 22 are all connected in parallel across a 15 V d.c. supply. The outputs from the emitters of each group of eight phototransistors are taken to corresponding inputs of respective multiplexers 24, 26 which are driven at a switching speed of 100 Khz by a clock generator 28 (FIG. 4) connected to a 4-bit counter 30, via lines 32. The output from each multiplexer is transmitted via a respective amplifier 34 or 36, along lines 38, 40 to a remotely positioned measuring circuit, FIG. 4.

The signals received from the two lines 38, 40 at the measuring circuit are applied to respective demultiplexers 42, 44 which are also driven by the lines 32 from the counter 30. Each output 46 corresponding to a respective phototransistor is fed to a network 48 which provides two outputs 50, 52 which are applied to the inputs of a comparator 54. The output 50 of the network is directly proportional to the instantaneous input signal on line 46, whilst the output 52 is averaged. A predetermined value is then determined from this averaged signal for comparison with the instantaneous signal. This predetermined value may, for example, correspond to 85% of the level of a "good" signal. Thus the comparator will give an output if the signal at 50 is less than 85% of the expected signal, and this output will be passed to the "set" input of a latch circuit 56 which will be switched so that it supplies a corresponding output to a respective input of one of a series of four NOR—gates 58 (it will be understood that there is one input corresponding to each phototransistor). The outputs of the NOR—gates are connected to the inputs of a four-input NAND-gate 60 whose output will therefore go "LO" in the event of a fault, driving a suitable fault indicator device (not shown) and operating a cigarette ejection facility.

In the example shown the main circuit elements are as follows:

| | |
|---|---|
| Optical sensor units (20,22): | Optron OPB 253A |
| Multiplexers/demultiplexers (24, 24, 42, 44); | |
| Transmission line drivers (34, 36); | LM 318 |
| Comparators (54): | LM 2901 |
| Latches (56): | 4044B |
| Gates (58, 60): | 14002, 14501 |
| Counter (30): | 14516 |

We claim:

1. An inspection device for a continuous cigarette rod comprising means for guiding a continuous cigarette rod along a predetermined path extending through an inspection station and a plurality of optical units arranged at the inspection station at circumferentially spaced positions around the path of the rod, each optical unit comprising a light emitter and a light detector, means associated with the emitter for focussing the emitted light from that emitter and directing the focussed light at a respective area of a rod being inspected, and means associated with the detector for collecting light reflected from the said area of the rod and for directing the collected light to the detector.

2. An inspection device according to claim 1 wherein the light emitter and the light detector of each unit are circumferentially spaced one from the other around the path of the rod.

3. An inspection device according to claim 1 or claim 2 wherein each optical unit is formed as an integral part, each unit including a first lens mounted to focus light from the emitter, and a second lens mounted to focus light impinging on the detector.

4. An inspection device according to claim 3 wherein the optical units are wedge shaped and are mounted to taper towards the inspection station.

5. An inspection device according to claim 1 or claim 2 wherein the optical units are arranged in at least two axially spaced circumferential arrays around the path of the rod at the inspection station, the units of each array being arranged to inspect areas of the rod which are staggered in relation to the areas inspected by the units of the other array.

6. An inspection device according to claim 1 including multiplexing means for transferring electrical signals from the detector of each optical unit to a control center.

7. An inspection device according to claim 1 including comparator means for detecting when the light intensity received by any one of the detectors falls below a predetermined value.

8. An inspection device according to claim 7 including a plurality of comparator means associated with respective optical units, and logic means for producing a signal to operate one of a cigarette ejection device and a warning device when any of the detectors receives a light intensity below said predetermined value.

9. An inspection device according to claim 7 or claim 8 including means for continually averaging the output signal of each detector and for determining said predetermined value in relation to that detector in dependence upon the averaged signal.

10. An inspection device according to claim 1 wherein the light emitters and detectors are infra-red devices.

11. An inspection device according to claim 1 wherein the means for guiding a cigarette rod is a transparant tube.

12. A method of inspecting cigarettes or other continuous rods of the tobacco industry comprising disposing a plurality of focussed light emitter-detector units at circumferentially-spaced positions around a rod being inspected, each unit being arranged to propagage focused light onto a defined surface region of the rod and to receive the light reflected from that surface region and further arranged to generate an electrical signal related to the intensity of the received light; multiplexing the intensity related signals from said units; transferring the multiplexed signals to a remote location; demultiplexing the signals at said remote location; and processing the signal from each unit by continually averaging the signal, comparing the averaged signal with the instantaneous signal from that unit, and generating a fault signal if the instantaneous signal differs from the averaged signals by more than a preset percentage.

13. An inspection device for a continuous cigarette rod comprising: a transparent tube for guiding the cigarette rod through an inspection region; and a plurality of infra-red units arranged in at least two arrays axially spaced along the inspection tube, the units of each array being circumferentially spaced one from another around the inspection tube, each unit comprising an infra-red emitter, a lens arranged to direct and focus a beam of infra-red radiation emitted by the emitter at a particular area of the rod, an infra-red detector and a lens arranged to collect light from that area and direct it to the detector, the areas inspected by units of each array being circumferentially staggered in relation to the areas inspected by units of the other array.

14. An inspection device for a continuous cigarette rod comprising means for guiding a continuous cigarette rod along a predetermined path extending through an inspection station; means including a plurality of light emitters for directing focused beams of light at circumferentially-spaced positions around said rod at said inspection station; means including a plurality of light detectors at circumferentially-spaced positions around the path of the rod at said inspectin station for detecting light from respective light emitters after reflection from said rod and for producing respective electrical signals representative thereof; multiplexing means for multiplexing the signals produced by said light detectors at said inspection station and for transmitting said multiplexed signals to a remote location; and control means at said remote location which is responsive to said multiplexed signals for generating a fault signal when any one of said multiplexed signals falls below a predetermined value.

15. An inspection device according to claim 14, wherein said light emitters and light detectors alternate with one another in a substantially common plane around said rod at said inspection station.

16. An inspection device according to claim 14 including means for continually averaging the output signal of each detector and for determining said predetermined value in relation to that detector in dependence upon the averaged signal.

* * * * *